United States Patent
Lemarie et al.

(10) Patent No.: US 11,772,325 B2
(45) Date of Patent: Oct. 3, 2023

(54) METHOD FOR PRODUCING A 3D-PRINTED TISSUE SUBSTITUTE

(71) Applicants: SEGULA ENGINEERING, Nanterre (FR); UNIVERSITE CLAUDE BERNARD—LYON 1, Villeurbanne (FR); CENTRE NATIONAL DE LA RECHERCHE SCIENTIFIQUE, Paris (FR)

(72) Inventors: Lucas Lemarie, Lyons (FR); Edwin-Joffrey Courtial, Villeurbanne (FR)

(73) Assignees: SEGULA ENGINEERING, Nanterre (FR); UNIVERSITE CLAUDE BERNARD—LYON 1, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 17/808,164

(22) Filed: Jun. 22, 2022

(65) Prior Publication Data

US 2022/0410472 A1   Dec. 29, 2022

(30) Foreign Application Priority Data

Jun. 24, 2021 (FR) ...................................... 2106791

(51) Int. Cl.
  *B29C 64/124*   (2017.01)
  *B33Y 10/00*   (2015.01)
  (Continued)

(52) U.S. Cl.
  CPC .......... *B29C 64/124* (2017.08); *B29C 64/209* (2017.08); *B29C 64/35* (2017.08);
  (Continued)

(58) Field of Classification Search
  None
  See application file for complete search history.

(56) References Cited

U.S. PATENT DOCUMENTS

| 2011/0041966 A1* | 2/2011 | Ishida | C23F 1/00 148/674 |
| 2016/0136326 A1* | 5/2016 | Fisher | A61L 27/507 264/494 |

(Continued)

FOREIGN PATENT DOCUMENTS

| CN | 111574816 A | 8/2020 |
| WO | 2016/090286 A1 | 6/2016 |

OTHER PUBLICATIONS

French Search Report received for Application No. 2106791, dated Feb. 9, 2022.

*Primary Examiner* — Mohammad M Ameen
(74) *Attorney, Agent, or Firm* — GREER BURNS & CRAIN LTD

(57) ABSTRACT

A method for producing a 3D-printed tissue substitute is disclosed, utilizing a 3D printing device including a tank including a yield stress fluid in which the material is printed, the printing material delivered by the cartridge includes polyvinyl alcohol and gelatin, the method including a step following which, after printing the material in the yield stress fluid, a printed intermediate device is solidified in the yield stress fluid by lowering the temperature of the tank. The intermediate device is removed from the tank, rinsed and dried in order to obtain the tissue substitute.

10 Claims, 3 Drawing Sheets

(51) Int. Cl.
*B33Y 70/00* (2020.01)
*B33Y 80/00* (2015.01)
*B29C 64/209* (2017.01)
*B29C 64/35* (2017.01)
*B33Y 40/20* (2020.01)
*B29K 29/00* (2006.01)
*B29K 105/00* (2006.01)
*B29K 105/24* (2006.01)
*B29L 31/00* (2006.01)

(52) U.S. Cl.
CPC ............... *B33Y 10/00* (2014.12); *B33Y 40/20* (2020.01); *B33Y 70/00* (2014.12); *B33Y 80/00* (2014.12); *B29K 2029/04* (2013.01); *B29K 2105/0061* (2013.01); *B29K 2105/24* (2013.01); *B29K 2995/0056* (2013.01); *B29L 2031/753* (2013.01)

(56) References Cited

U.S. PATENT DOCUMENTS

2017/0361534 A1* 12/2017 Fernandez-Nieves ....................... B29C 64/106
2018/0304537 A1* 10/2018 Rubinsky ............... B29C 64/106
2019/0275746 A1* 9/2019 Huang .................... B29C 64/40
2020/0032004 A1* 1/2020 Hudson .................. C09D 11/04

* cited by examiner

[Fig. 1]
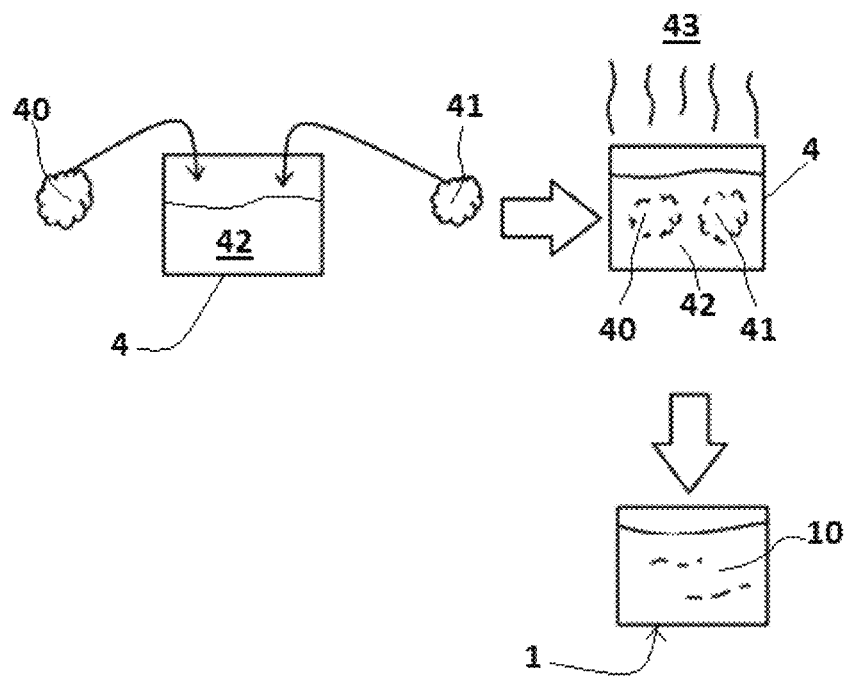
[Fig. 2]
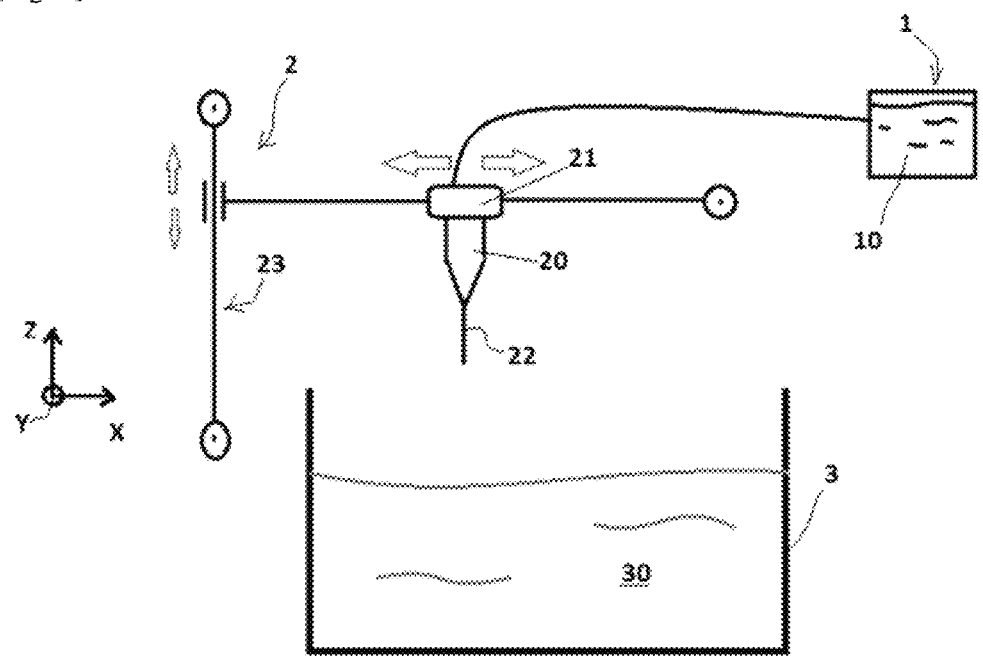

[Fig. 3]
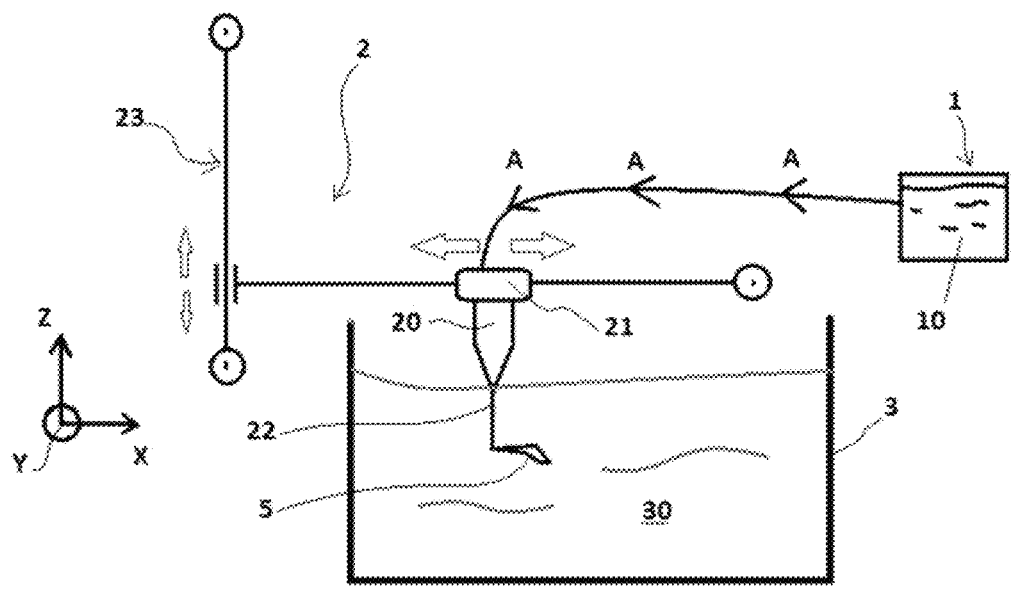
[Fig. 4]
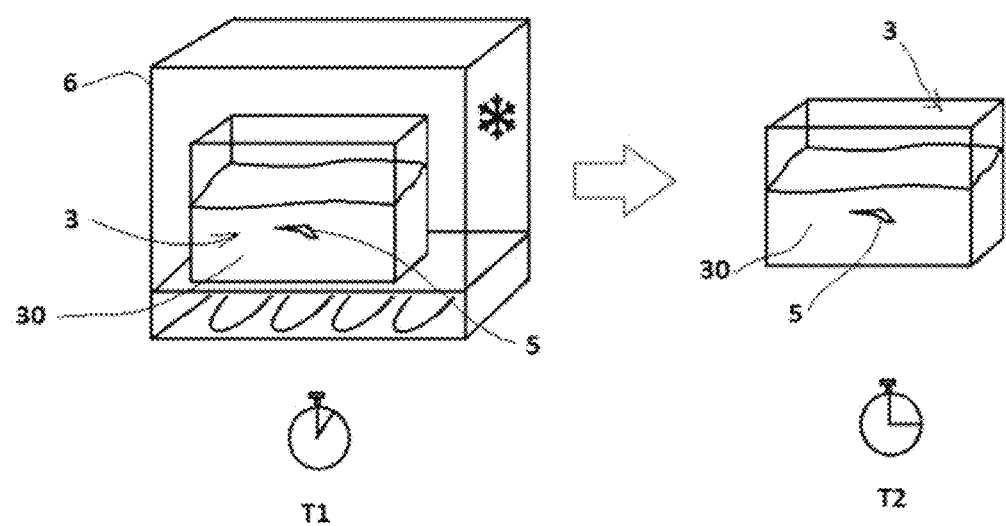

[Fig. 5]
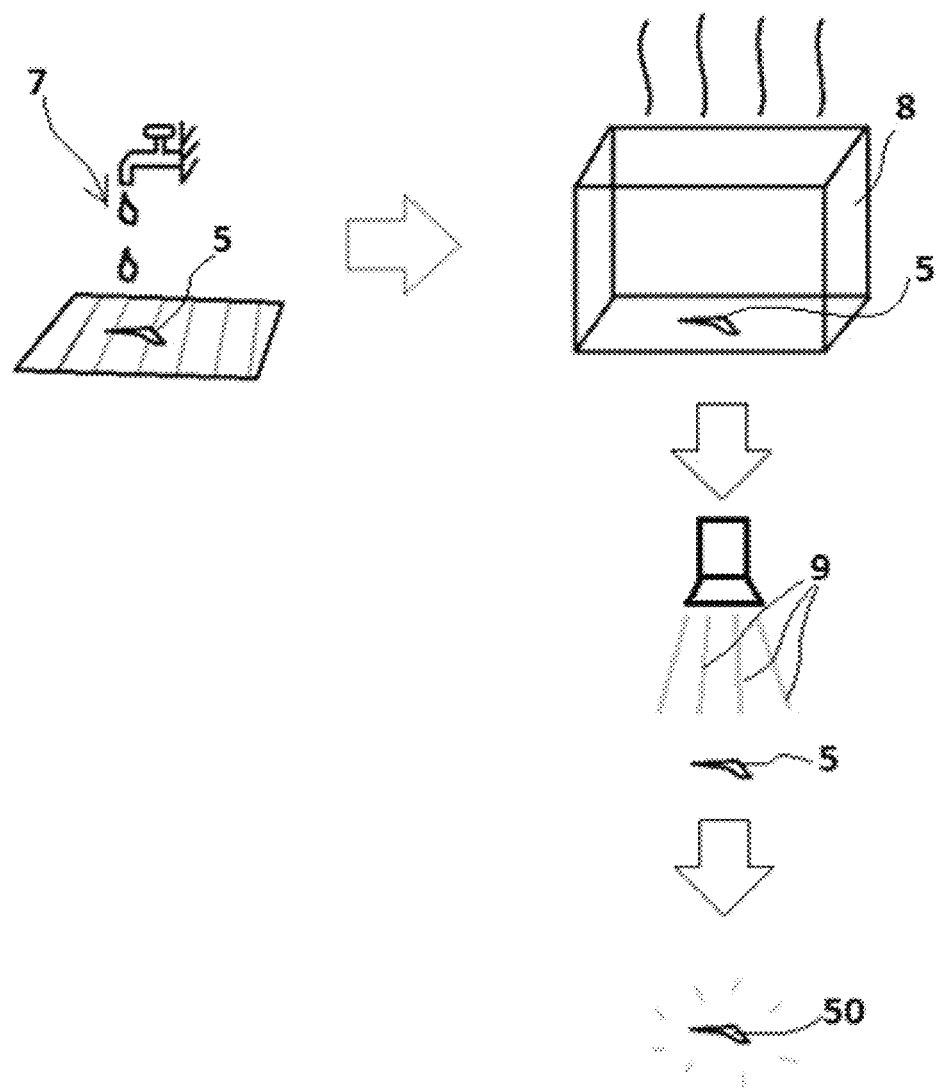

METHOD FOR PRODUCING A 3D-PRINTED TISSUE SUBSTITUTE

BACKGROUND

The invention relates to the production of a tissue substitute by 3D printing intended to be implanted in a human body.

Currently, medical devices intended to be implanted in the human body (stents, endoprosthesis, vascular prothesis, etc.) are preferably produced from biomaterial in order to allow the organ or the organ part temporarily replaced to regenerate in situ.

Methods for manufacturing such devices by moulding are known and the material used is for example polyvinyl alcohol (or PVAL) or polyethylene glycol. Polyvinyl alcohol may be combined in certain compositions with sodium trimetaphosphate and with gelatin in order to make it possible to produce a device by moulding.

Devices produced by 3D printing such as those described in document WO 2016/090286 are also known. The method utilizes a 3D printing device comprising a print head equipped with at least one cartridge for delivering is printing material, said device including a tank comprising a yield stress fluid in which said material is printed, said print head being mounted mobile in displacement out of said tank and into said tank.

In order to obtain the tissue substitute, it is necessary to apply a chemical and physical treatment after the 3D printing in order to set the shape of the printed device by cross-linking and solidification: this is obtained by applying a UV light radiation or by thermogelling methods.

The drawback of such a method is that it utilizes a chemical treatment which can make the device potentially cytotoxic.

SUMMARY

The invention aims to propose a method which requires no chemical treatment in order to produce the tissue substitute.

To this end, the invention relates to a method for producing a 3D-printed tissue substitute, utilizing a 3D printing device comprising a print head equipped with at least one cartridge for delivering printing material, said device including a tank comprising a yield stress fluid in which said material is printed, said print head being mounted mobile in displacement, said printing material solidifying substantially at a first solidification temperature and said yield stress fluid solidifying substantially at a second solidification temperature.

The method according to the invention is notable in that said printing material delivered by the cartridge includes polyvinyl alcohol and gelatin, in that said second solidification temperature of the yield stress fluid is lower than said first solidification temperature of said printing material and in that said method comprises the following steps:
  solubilizing said printing material so as to obtain a sufficiently fluid material so that it is delivered by said cartridge,
  supplying said 3D printing device with said solubilized material,
  printing said material in said yield stress fluid in the tank by displacing is the print head into said tank and delivery of said material by said cartridge so as to form an intermediate device,
  solidifying said intermediate device by placing said tank at a temperature lower than said first solidification temperature for a first time interval, said temperature however being higher than said second solidification temperature, then by placing the tank at ambient temperature for a second time interval, the ambient temperature being higher than said first and second temperatures,
  removing said solidified intermediate device from said tank,
  rinsing said solidified intermediate device, and
  drying said intermediate device in order to obtain said tissue substitute.

By selecting a yield stress fluid the solidification temperature of which is lower than the solidification temperature of the printing material and by using the cross-linking properties of polyvinyl alcohol at low temperatures, the method thus makes it possible to create a tissue substitute from 3D-printed biomaterial without chemical cross-linking via the photonic (UV) route, which prevents making the tissue substitute cytotoxic.

The method according to the invention may also comprise the following characteristics, independently or in combination:

Advantageously, said printing material includes substantially between 10 and 25% by weight polyvinyl alcohol (or between 10 and 25% by weight polyvinyl alcohol) and substantially between 0.5 and 2% by weight gelatin (or between 0.5 and 2% by weight gelatin), preferably substantially 20% by weight polyvinyl alcohol (or 20% by weight polyvinyl alcohol) and substantially 1% by weight gelatin (or 1% by weight gelatin).

In the context of an advantageous embodiment, the yield stress fluid includes substantially at least 80% by weight ethanol (or at least 80% by weight ethanol) and substantially between 2 and 5% by weight of a cross-linked acrylic acid synthetic polymer (or between 2 and 5% by weight of a cross-linked acrylic acid synthetic polymer) marketed under the name of Carbopol® (940), preferably substantially 3.5% by weight (or 3.5% by weight).

More preferably, the solubilization of said printing material is carried out is at a temperature comprised substantially between 90° C. and 100° C. (or between 90° C. and 100° C.).

Moreover, said solidification of said intermediate device is carried out at a temperature comprised substantially between −5° C. and −90° C. (or between −5° C. and −90° C.), preferably at substantially −80° C. (or at −80° C.).

Advantageously, said solidification is carried out by placing said tank at said solidification temperature in a refrigerated cabinet for substantially 1 hour, then by leaving the tank at ambient temperature for substantially 3 hours.

In order to make it possible to simulate an aging of the created tissue substitute, the solidification step may be repeated at least twice.

Preferably, the drying is carried out by lyophilization of the intermediate device during a lyophilization time such that the tissue substitute obtained at the end of said lyophilization time comprises less than 3% by weight water.

Moreover, according to an embodiment to be described hereinafter, the method includes a final step of decontaminating said tissue substitute, for example by subjecting said tissue substitute to a decontaminating radiation (in order for the device not to have to come into contact with a potentially cytotoxic fluid).

The invention also relates to a tissue substitute obtained by said method as defined above.

BRIEF DESCRIPTION OF THE DRAWINGS

Other advantages and characteristics of the invention will become apparent on examination of the detailed description of an embodiment which is in no way limitative, and from the attached drawings, in which:

FIG. 1 is a diagrammatic representation of a step of a method according to the invention, FIG. 2 is another diagrammatic representation of a 3D printing device and a tank utilized in a step of a method according to the invention, FIG. 3 is a diagrammatic representation of the device and the tank shown in FIG. 2, utilized according to another step of a method according to the invention, FIG. 4 shows yet another step of a method according to the invention, FIG. 5 shows a final step of a method according to the invention.

DETAILED DESCRIPTION

The equipment utilized in the method according to the invention is shown in the figures.

FIG. 1 shows a reservoir 1 containing a printing material 10.

FIGS. 2 and 3 show a 3D printing device 2, including a print head 21 which is equipped with a cartridge 20 for delivering the printing material 10, the print head 21 being supplied with printing material 10 by the reservoir 1.

The cartridge 20 is equipped with a needle 22, through which the printing material 10 is delivered.

FIGS. 2 and 3 also show a tank 3, placed under the print head 21 of the 3D printing device 2.

The tank 3 contains a yield stress fluid 30.

The print head 21 of the 3D printing device 2 is mounted mobile in displacement on a frame 23 in three directions X, Y and Z, which ensures the displacement of the print head 21 out of the tank and into the tank 3 in order to make it possible to 3D print a tissue substitute in the yield stress fluid 30.

According to the invention, the printing material 10 and the yield stress fluid 30 are selected such that the solidification temperature of the printing material 10 is greater than the solidification temperature of the yield stress fluid 30: in other words, by lowering the temperature, the printing material 10 will be the first to solidify from the printing material 10 and the yield stress fluid 30.

In yet other words, the solidification temperature of the yield stress fluid 30 is lower than the solidification temperature of the printing material 10. Furthermore, the printing material is a biomaterial, i.e. a material which is degrades in order to allow the organ or the organ part temporarily replaced by this material to regenerate in situ.

In the context of this implementation example of a method according to the invention, the printing material includes polyvinyl alcohol and gelatin. According to the invention, the quantity of polyvinyl alcohol in the printing material 10 is comprised between 10 and 25% by weight, or substantially comprised between 10 and 25% by weight, and the quantity of gelatin in the printing material 10 is comprised between 0.5 and 2% by weight, or substantially comprised between 0.5 and 2% by weight.

FIG. 1 shows (diagrammatically) the production of the printing biomaterial 10.

In the context of this specific example, the printing biomaterial 10 includes 20% by weight polyvinyl (or substantially 20% by weight), 1% by weight gelatin (or substantially 1% by weight), the third ingredient being ultrapure water (also known as "Milli-Q water" or "UPW") present at 79% by weight (or substantially 79% by weight).

Thus, 20 g polyvinyl alcohol 40, 1 g gelatin 41 and 79 g Milli-Q water 42 are mixed in a vessel 4.

Then, the mixture is solubilized in order to produce the printing material 10. To this end, the recipient is placed at a temperature 43 comprised between 90° and 100° (or substantially comprised between 90° and) 100°, preferably at 90° (or substantially 90°).

The solubilization step makes it possible to obtain a printing material 10 which is sufficiently fluid in order to be delivered by the cartridge 20 through the needle 22.

The gelatin 41 is a type A porcine gelatin. Generally, gelatin originating from an animal, of the medical type and intended for laboratory use is selected.

In the context of this example, adding a dye to the printable material is intended: in fact, the tank 3, the yield stress fluid 30 and the printing biomaterial 10 are all three transparent. If it is desirable to observe the object being 3D printed in the yield stress fluid 30, it is preferable to add is a dye to the printing biomaterial.

Thus, the 3D-printed device is more easily viewed and it is simpler to monitor its production and to grip it in order to remove it from the tank 3. It should be noted that the solidification temperature of the printing biomaterial (or printing material 10) is substantially 0° C. In fact, it is the water molecules present in the biomaterial which the method looks to solidify. Thus, once the biomaterial is placed at a temperature below 0° C., the desired solidification is obtained. The lower the temperature below 0, the faster the solidification takes place.

The cryo-crosslinking is initiated as soon as the crystals are formed by solidification of the water contained in the biomaterial. Thus, the tissue substitute is obtained in this way.

The yield stress fluid 30 includes 80% by weight ethanol (or substantially 80% by weight ethanol), pure water and between 2 and 5% by weight (or substantially between 2 and 5% by weight) of a gelling agent including a cross-linked acrylic acid synthetic polymer marketed under the name of CARBOPOL® (Carbopol 940).

More specifically, the quantity of CARBOPOL® is 3.5% by weight (or substantially 3.5% by weight).

The yield stress fluid 30 obtained is therefore in the form of a gel.

The solidification temperature of the yield stress fluid is below −80° C.: it is substantially −100° C.

FIG. 3 diagrammatically shows the 3D printing of an intermediate device 5 in the yield stress fluid 30 by the printing device 2.

To this end, the 3D printing device 2 is supplied with solubilized printing material 10 (this supply is represented by the arrows A).

The printing is ordered and the 3D printing device 2 prints the intermediate device in the yield stress fluid 30 by displacing the print head 21 on the frame 23 according to a predetermined programme which depends on the shape desired to be given to the intermediate device 5 and its dimensions.

In order to allow a good insertion of the needle 22 into the yield stress fluid 30, a needle having a length of at least 5 cm is intended.

The yield stress fluid 30 forming a gel holds the printed filament in position: the printed intermediate device is thus held in suspension by the yield stress fluid 30 in the tank 3.

Once the intermediate device 5 is produced and according to the invention, it is solidified in order to set its shape.

To this end, as shown diagrammatically in FIG. 4, the tank 3 is placed in a refrigerated cabinet 6 such as a freezer, where the temperature is at least −5° C.

It should be noted that the temperature of the refrigerated cabinet must however remain above the solidification temperature of the yield stress fluid which must itself remain liquid or viscous in order to make it possible to remove the intermediate device 5, once the intermediate device 5 is solidified.

In the context of this example, the tank 3 is placed for approximately one hour (time interval T1) at a temperature of −80° C. (according to the invention, the tank must be placed at a temperature comprised between −5° C. and −90° C. for a first time interval).

During the time interval T1, the intermediate device 5 solidifies: in fact, the temperature of the cabinet 6 forces the intermediate device to freeze and the mechanical pressure applied by the freezing of the intermediate device 5 ensures the creation of a solid bond between the molecules of the material 10 which will remain even after unfreezing the device.

Thus, after the time interval T1, the tank 3 is removed from the refrigerated cabinet 6 and the tank is left at ambient temperature (temperature of the room in which the method is implemented, above the solidification temperature of the intermediate device) for a second time interval T2 of substantially three hours.

The second time interval T2 is therefore greater (at least twice) than the first time interval T1.

In the context of this embodiment, the solidification step is thus carried out during a cycle comprising the first time interval T1 of solidification and the second time interval of bringing to ambient temperature.

It is possible to carry out this solidification step by carrying out several is cycles: after a first cycle (T1 at a temperature of −80° C. and T2 at ambient temperature), it is possible to restart the solidification operation at T1 (−80° C.) followed by T2 (at ambient temperature).

Carrying out several cycles makes it possible to simulate the aging of the tissue substitute, so that it corresponds to the age of the element of the body in which it is intended to be implanted.

In fact, by carrying out several successive cycles, a condition of the device is simulated. Thus, if the tissue substitute to be created is intended for a person in their twenties for example, a single cycle will be needed. It is also possible to envisage carrying out four successive cycles so that the condition of the tissue substitute 50 is close to the condition of an artery of a patient who is 60 years old for example.

In fact, by carrying out several successive cycles, the degree of crystallinity of the tissue device is increased, which results in a rigidification and a loss of elastic properties of the tissue substitute.

After the cycle ensuring the solidification of the intermediate device 5, removal of the intermediate device 5 from the tank is carried out (by gripping it manually or with a utensil) and a rinsing 7 of the intermediate device 5 is carried out (see FIG. 5).

Then, drying the device 5 is intended.

Open air drying may be envisaged.

Drying by lyophilization is preferred to any other type of drying in order to best maintain the shape of the device obtained: to this end, the intermediate device 5 is placed in a lyophilization chamber 8 utilizing a vacuum pump; during a lyophilization time which is such that the intermediate device 5 obtained only contains at most 3% water.

The device obtained is therefore better preserved until its rehydration before implanting into the human body.

Finally, in order to ensure that no contaminating agent develops on the device, decontamination thereof is intended by projecting a decontaminating light radiation 9 of the ultraviolet type thereon.

A tissue substitute 50 according to the invention is therefore obtained at the end of all the aforementioned steps.

It is understood from the preceding description how the invention makes it possible to produce a tissue substitute 50 from biomaterial and printed in 3D in a safe, simple and fast way.

It is also understood how the invention makes it possible to produce tissue substitutes which are adapted to the age of the patients, as the method makes it possible to produce tissue substitutes that are more or less "worn" and corresponding to the condition of the tissues of the patient in question.

It should be understood that the invention is not limited to the implementation of the method specifically described above and that it extends to the implementation of any equivalent means.

While a particular embodiment of the present method for producing a 3d-printed tissue substitute have been described herein, it will be appreciated by those skilled in the art that changes and modifications may be made thereto without departing from the invention in its broader aspects and as set forth in the following claims.

The invention claimed is:

1. A method for producing a 3D-printed tissue substitute, utilizing a 3D printing device comprising a print head equipped with at least one printing material delivery cartridge, said 3D printing device including a tank comprising a yield stress fluid, forming a gel in which said material is printed, said print head being mounted mobile in displacement, said printing material solidifying substantially under a first solidification temperature and said yield stress fluid solidifying substantially under a second solidification temperature, said method includes printing material delivered by the cartridge includes polyvinyl alcohol and gelatin, in that said second solidification temperature of the yield stress fluid is lower than said first solidification temperature of said printing material, and in that said method includes the following steps:
   solubilizing said printing material so as to obtain a sufficiently fluid material so that it is delivered by said cartridge;
   supplying said 3D printing device with said solubilized material;
   printing said material in said yield stress fluid in the tank by moving the print head into said tank and delivery of said material by said cartridge so as to form an intermediate device;
   solidifying said intermediate device by placing said tank at a temperature lower than said first solidification temperature for a first time interval (T1), said temperature however being higher than said second solidification temperature, then by placing the tank at ambient temperature for a second time interval (T2), said ambient temperature being higher than said first and second solidification temperatures;

removing said solidified intermediate device from said tank;

rinsing said solidified intermediate device; and drying said intermediate device in order to obtain said tissue substitute.

2. The method according to claim 1, characterized in that said printing material includes substantially between 10 and 25% by weight polyvinyl alcohol and substantially between 0.5 and 2% by weight gelatin.

3. The method according to claim 1, characterized in that the yield stress fluid includes substantially at least 80% by weight ethanol and substantially between 2 and 5% by weight of a cross-linked acrylic acid synthetic polymer.

4. The method according to claim 1, characterized in that said solubilization of said printing material is carried out at a temperature comprised between substantially 90° C. and 100° C.

5. The method according to claim 1, characterized in that said solidification of said intermediate device is carried out at a temperature comprised substantially between −5° C. and −90° C.

6. The method according to claim 1, characterized in that said solidification is carried out by placing said tank at said solidification temperature in a refrigerated cabinet for substantially 1 hour (T1), then by leaving the tank at ambient temperature for substantially 3 hours (T2).

7. The method according to claim 1, characterized in that the solidification step is repeated at least twice.

8. The method according to claim 1, characterized in that the drying is carried out by lyophilization of the intermediate device during a lyophilization time such that the tissue substitute obtained at the end of said lyophilization time comprises less than 3% by weight water.

9. A process according to claim 1, characterized in that it includes a final step of decontamination of said tissue substitute.

10. The process according to claim 9, characterized in that said decontamination step is carried out by subjecting said tissue substitute to decontaminating radiation.

* * * * *